(12) United States Patent
Botruff et al.

(10) Patent No.: US 6,272,767 B1
(45) Date of Patent: Aug. 14, 2001

(54) ENVIRONMENTAL TEST CHAMBER

(75) Inventors: Dwayne D. Botruff, Caledonia; Gregory J. Langfeldt, Kentwood, both of MI (US)

(73) Assignee: Envirotronics, Inc., Kentwood, MI (US)

( * ) Notice: Subject to any disclaimer, the term of this patent is extended or adjusted under 35 U.S.C. 154(b) by 0 days.

(21) Appl. No.: 09/422,320

(22) Filed: Oct. 21, 1999

(51) Int. Cl.$^7$ ..................................................... F26B 19/00
(52) U.S. Cl. ................................. 34/202; 34/204; 34/210; 34/215; 34/225; 34/227; 454/57; 454/187; 454/229
(58) Field of Search ............................... 34/202, 204, 209, 34/210, 215, 218, 225, 227; 454/57, 58, 187, 228, 229, 236

(56) References Cited

U.S. PATENT DOCUMENTS

| | | | |
|---|---|---|---|
| 4,420,679 | * 12/1983 | Howe | 219/400 |
| 5,851,143 | * 12/1998 | Hamid | 454/57 |
| 6,005,404 | * 12/1999 | Cochran et al. | 324/760 |

OTHER PUBLICATIONS

Envirotronics environmental test equipment, 1981.
Envirotronics environmental test equipment, 1984.
*Envirotronics Today*, 1986.
Envirotronics environmental test chambers, 1987.
Envirotronics environmental test chambers, 1993.

* cited by examiner

*Primary Examiner*—Pamela Wilson
(74) *Attorney, Agent, or Firm*—Van Dyke, Gardner, Linn & Burkhart, LLP

(57) ABSTRACT

An environmental test chamber comprises a first chamber and a second chamber separated by a partition. The first chamber receives one or more electronic components to be tested. The first chamber includes an exhaust area through which air is introduced to the first chamber and an intake area from which air is evacuated from the first chamber. The exhaust area and intake area are both fitted with a panel having a plurality of apertures. The size and/or the distance between the apertures is varied to provide a uniform airflow through the first chamber, thereby insuring that each electrical component housed within the first chamber experiences the desired temperature and humidity conditions. An air intake assembly is provided which draws air into a control panel chamber housing the electrical circuitry necessary to operate the environmental test chamber, and transports the air into the second chamber to thereby permit both the control panel chamber and the second chamber to receive ambient air. An air manifold is positioned below the partition and injects dry, compressed air upward through the partition to thereby pressurize the same. Pressurization of the partition assures that heated air and/or moisture residing within the first chamber does not migrate into the second chamber and thus avoids thermal and humidity gradients within the first chamber.

50 Claims, 16 Drawing Sheets

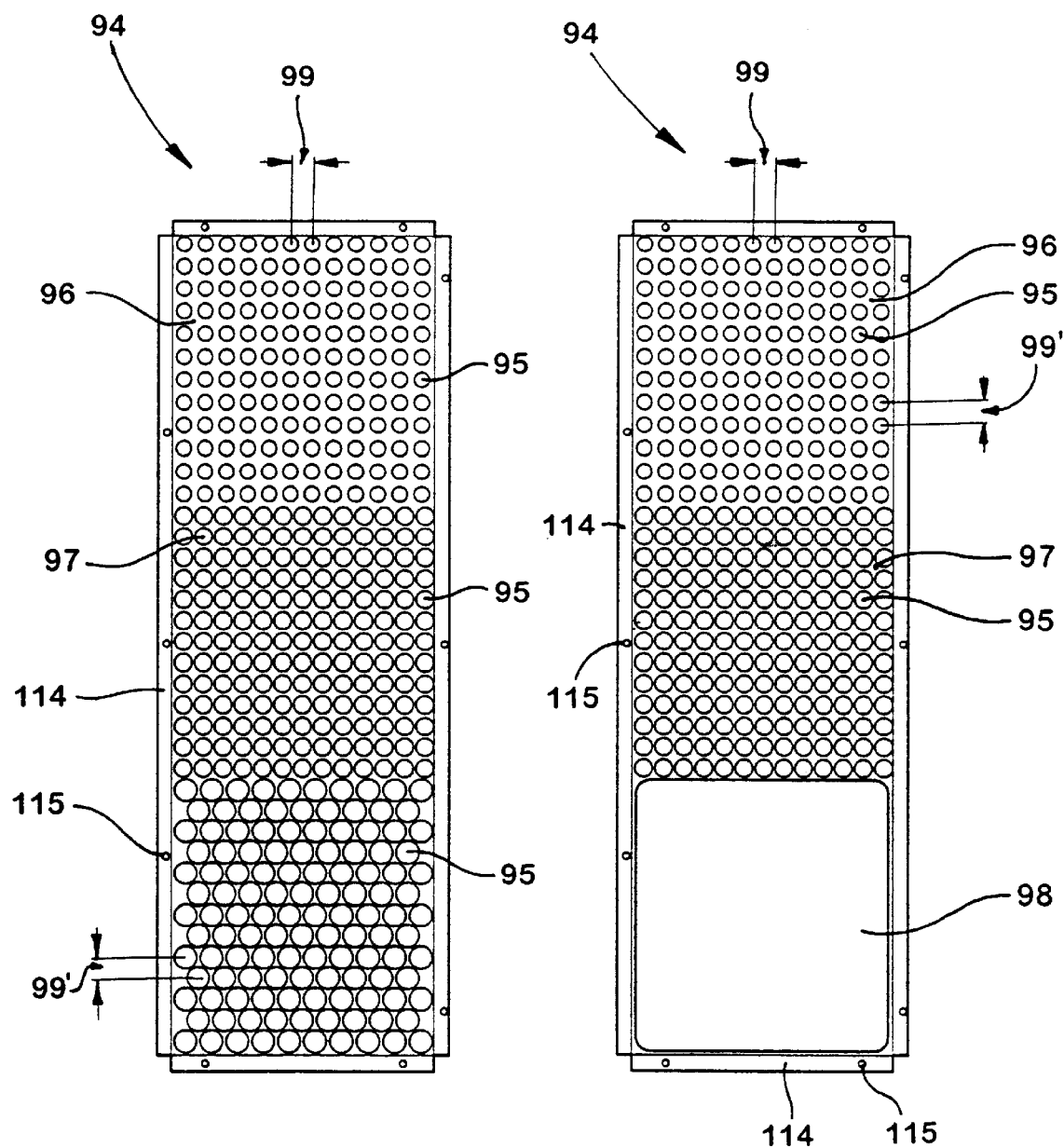

ENVIRONMENTAL TEST CHAMBER

BACKGROUND OF THE INVENTION

The invention relates generally to environmental test chambers. In particular, the present invention relates to environmental test chambers for thermal and humidity cycling of components. The invention is especially adapted for use in testing electronic components, but may find other applications.

Environmental test chambers are frequently utilized in order to test a variety of devices. Electrical components, and in particular, computer hard drive data storage units are normally tested in an environmental test chamber in order to assure that the hard drive can operate under pre-selected temperature and humidity conditions frequently encountered during its use.

In one common design, an environmental test chamber used to test computer hard drives includes a housing having a main or first chamber, and an auxiliary or second chamber separated by a partition. The hard drives are stacked within the first chamber in a pre-selected array. The central processing units, or CPU's, responsible for controlling the operation of the hard drives, are positioned within the second chamber. The CPUs and hard drives are maintained in electrical connection by one or more electrical cables passing through the partition.

One common type of partition that may be used to separate the chambers is composed of a plurality of foamed polymeric or ceramic bricks, provided with throughholes dimensioned to enable an electrical cable to pass therethrough. Alternatively, the electrical cables may be passed through the interstitial areas between the bricks. The partition attempts to provide a sealed wall between the chambers such that the temperature and humidity conditions of one chamber does not alter the temperature and humidity conditions of the other chamber.

In operation, the first chamber is loaded with hard drives in a pre-selected spatial arrangement, while the CPUs are placed in the second chamber and separated from the main chamber by the partition. The hard drives positioned within the first chamber are exposed to an airflow of varying temperature and humidity, according to a pre-selected temperature and humidity schedule. Specifically, the treated air is introduced to the first chamber through an exhaust area, is drawn through and about the hard drives, and is evacuated therefrom at an intake area. Once evacuated from the interior of the first chamber, the air is treated to assure that the air re-entering the first chamber conforms to the preselected temperature and humidity schedule. Thereafter, the air is recirculated to the first chamber. The control units, or CPUs, positioned in the secondary chamber are maintained at room temperature, or slightly above, and normal humidity conditions so as not to overheat. During testing, the CPUs command the hard drives to execute certain operations in order to verify acceptable performance of the hard drives under varying temperature and humidity conditions.

One problem frequently encountered by existing environmental test chambers is inadequate, non-uniform airflow through the first chamber. The purpose of environmental testing is to determine whether a particular unit, such as an electrical component, will operate in a sufficient manner under preselected temperature and humidity conditions. Consequently, in order to determine whether the unit actually performs sufficiently under the preselected criteria, each unit should receive approximately the same airflow so that it experiences the preselected temperature and humidity conditions. However, existing environmental test chambers often experience airflow gradients within the first chamber. These airflow gradients, in turn, generate thermal and humidity gradients. Failure to establish a uniform airflow throughout the first chamber results in ineffective and inaccurate testing of the hard drives or other electrical components positioned within the environmental test chamber.

Additionally, most environmental test chambers are provided with an electrical control panel chamber which supports the electrical devices and circuitry necessary to operate the environmental test chamber. In most circumstances, this control panel chamber is carried by the housing and is external to both the first chamber and the second chamber. Given the elevated temperatures at which environmental test chambers are operated, the control panel chamber often becomes hot, and must be supplied with a quantity of ambient air to cool the electrical devices. The ambient air is drawn into the control panel chamber through a separate air intake assembly from that which draws ambient air into the second chamber to cool the CPUs. An air exhaust assembly evacuates air from the control panel chamber. The control panel chamber air exhaust assembly is also separate from the air exhaust assembly governing the removal of air from the second chamber. The necessity for two separate air intake and exhaust assemblies is inefficient and increases manufacturing and operation costs.

Still another problem confronted by the industry is the inability of existing environmental test chambers to provide an effective barrier or partition between the first chamber and the second chamber. As the partition is usually a plurality of tiles or bricks stacked in a vertical array, interstitial spaces between these bricks enables the migration of air between the chambers. As a result, the humid, heated air, or cooled air, positioned within the first chamber will escape into the second chamber, resulting in deleterious consequences. First, increased humidity levels within the second chamber may damage the CPUs. Furthermore, migration of air to and from the first chamber generates a thermal and humidity gradient in proximity to the partition and consequently reduces the effectiveness of any test conducted therein.

Accordingly, there exists a need for an environmental test chamber capable of providing a uniform airflow through the first chamber. There is also a need for an environmental test chamber which can efficiently draft both the control panel chamber and the second chamber, and also, provide a sealed barrier between the first chamber and the second chamber.

SUMMARY OF THE INVENTION

The present invention overcomes the difficulties confronted by the prior art by advancing an environmental test chamber which provides a uniform airflow within the first chamber such that each unit under test is exposed to the desired temperature and humidity level. Also, the environmental test chamber of the present invention is configured to circulate ambient air through both the control panel area and the second chamber, and provides an effective partition between the first and second chambers such that temperature and humidity conditions within each chamber are maintained.

According to an aspect of the invention, an environmental chamber includes a housing positioned a preselected distance above the floor by a support. The housing defines a main or first chamber into which computer hard drives or other electrical components are positioned in a preselected array. The first chamber includes an exhaust region through which treated air is introduced to the first chamber and an intake region wherefrom air is evacuated. The exhaust region and the intake region are configured to provide a substantially uniform airflow across the vertical cross section or height of the first chamber.

In a preferred form, a uniform airflow is established within the first chamber by an exhaust panel and an intake panel positioned within the exhaust region and intake region, respectively. Both the exhaust and intake panel are formed with a plurality of apertures the size of which, and/or the horizontal or vertical distance between, is varied to provide a uniform laminar airflow into and out of the first chamber. Configuring the intake and exhaust regions of the first chamber to provide a substantially uniform airflow minimizes the occurrence of thermal and moisture gradients and assures that each hard drive or electrical component positioned therein will experience approximately the same temperature and humidity conditions.

According to another aspect of the invention, the environmental test chamber includes a first chamber separated from a second chamber by a partition. The housing is further provided with a control panel chamber external to both the first and second chamber. An air intake assembly is positioned in both the control panel chamber and the second chamber, enabling air to be drawn into the control panel chamber, across the electrical circuitry, and subsequently forwarded into the second chamber. Once the air is drawn through the CPU's placed within the second chamber, it is vented to the atmosphere by one or more blowers or fans positioned in the second chamber. Providing an air intake assembly capable of drawing air into both the control panel area and the second chamber eliminates the need for separate fans in both the control panel area and second chamber, and hence, reduces both operation and manufacturing costs.

According to another aspect of the invention, the partition separating the first and second chamber is formed of a plurality of foamed polymeric or composite bricks stacked in a vertical arrangement. The opposing sides, top and bottom of each brick are provided with a cut-out section such that when placed in relation to an adjacent brick, the cut-out sections are in registration. The environmental test chamber further includes an air manifold positioned below the partition. The air manifold contains a plurality of throughholes, each of which is positioned in registration with the cut-out sections of the bricks. The air manifold injects pressurized, heated air into the cut-out sections between the bricks to thereby pressurize the partition. Pressurization between the bricks prevents air migration between the chambers via the interstitial spaces defined between the bricks. Consequently, temperature and humidity conditions within both chambers is maintained. Maintenance of environmental conditions within the first chamber reduces the potential for localized thermal and humidity gradients in proximity to the partition, and thereby increases the effectiveness of the environmental testing. Furthermore, prohibiting moisture from entering the second chamber protects the CPUs from damage.

In an alternative preferred embodiment, the partition is a one-piece panel having a plurality of interconnected horizontal and vertical channels formed therein. These horizontal and vertical channels form an internal lattice, allowing pressurized, heated air from the air manifold to pressurize and maintain the panel at a preselected temperature, and thereby prevents the exchange of air and moisture between the chambers.

These and other objects, advantages and features of this invention will become apparent upon review of the following specification in conjunction with the drawings.

BRIEF DESCRIPTION OF THE DRAWINGS

FIG. 8 is a front view of an intake panel according to the invention;

FIG. 9 is a front view of an intake panel according to an alternative preferred embodiment f the invention;

DETAILED DESCRIPTION OF THE PREFERRED EMBODIMENTS

Figure 1:
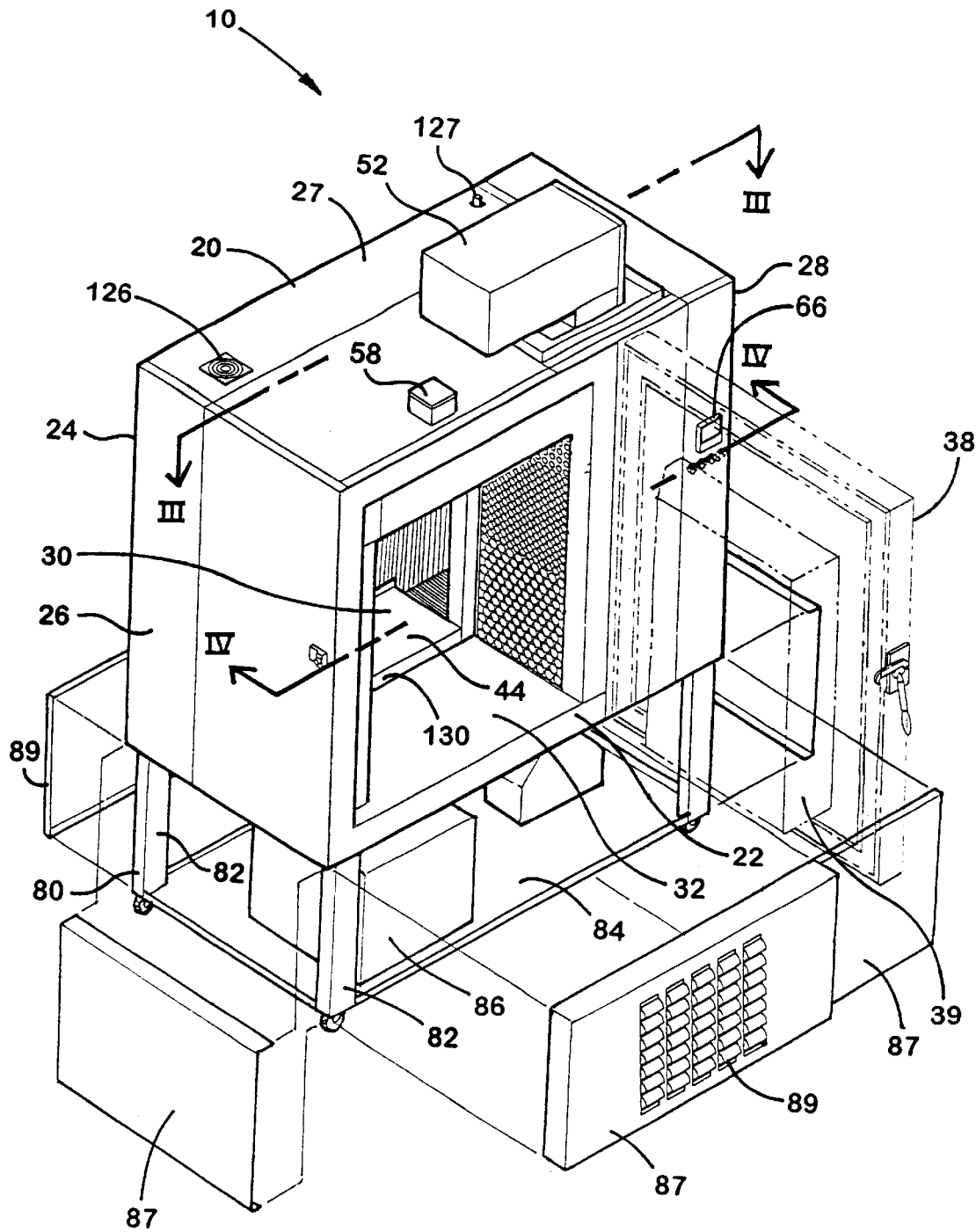
FIG. 1 is a front, partially exploded perspective view of an environmental test chamber according to the present invention.
Figure 2:
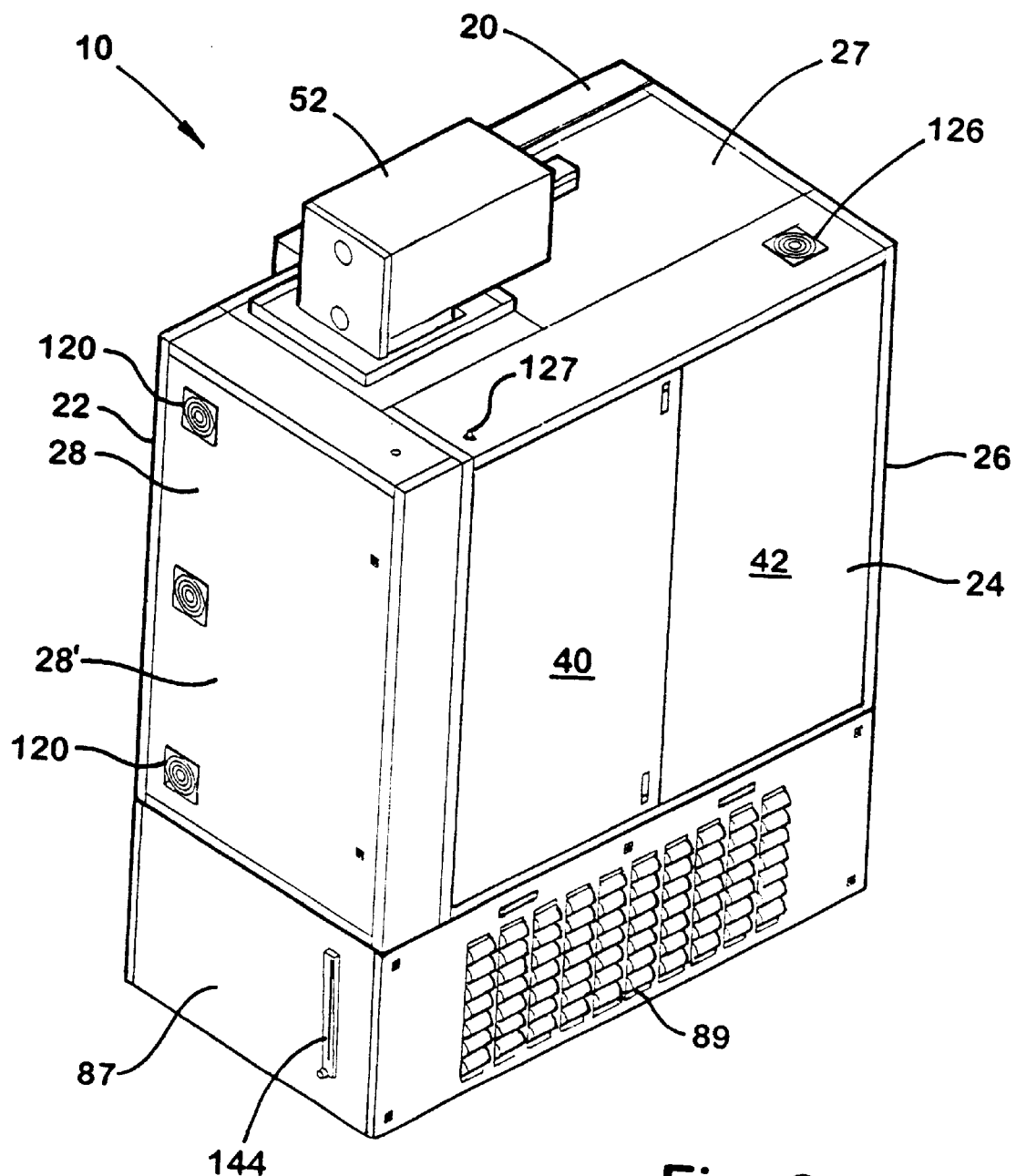
FIG. 2 is a rear perspective view of the environmental test chamber depicted in FIG. 1.
Figure 3:
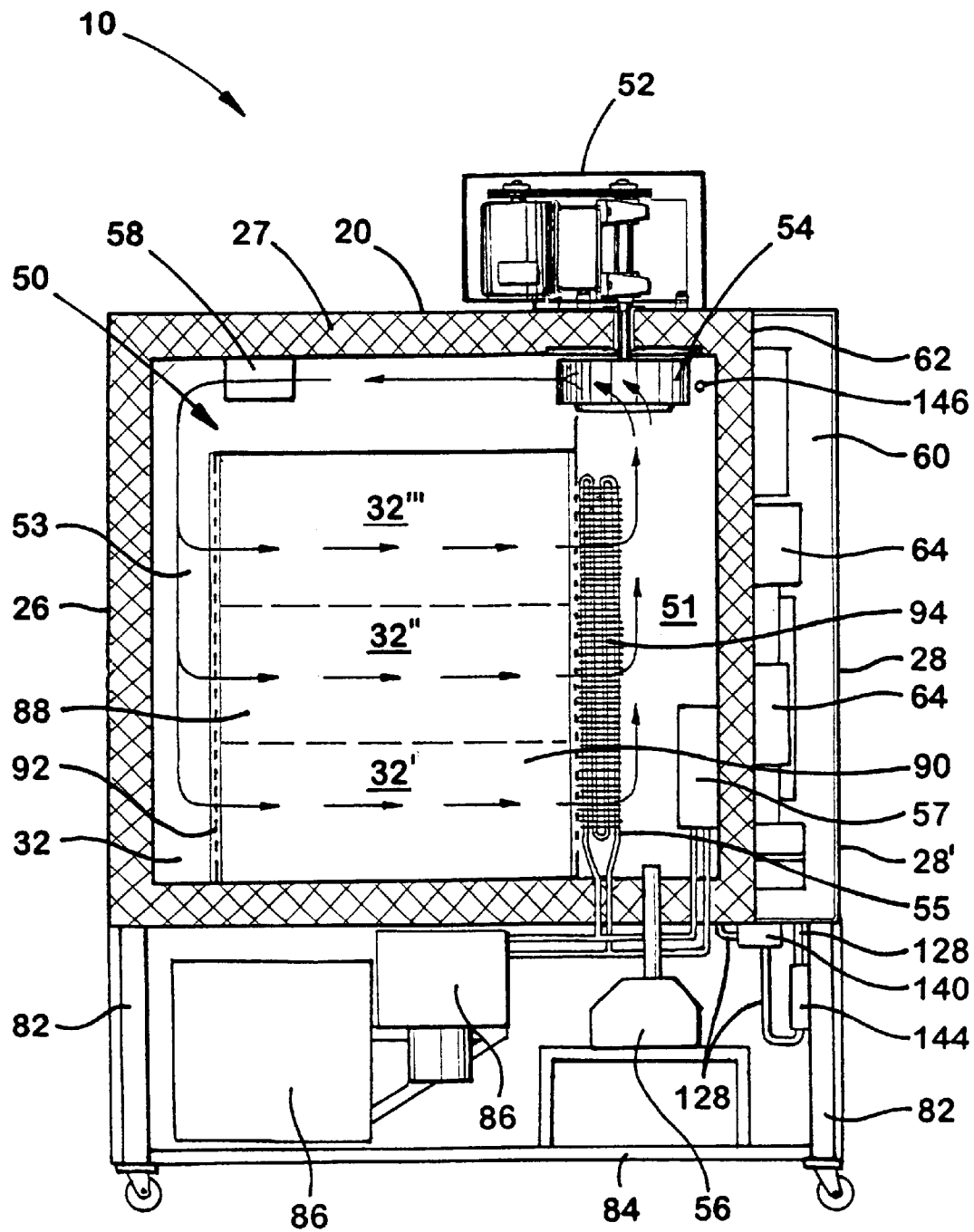
FIG. 3 is a sectional view taken along line III—III of FIG. 1.
Figure 4:
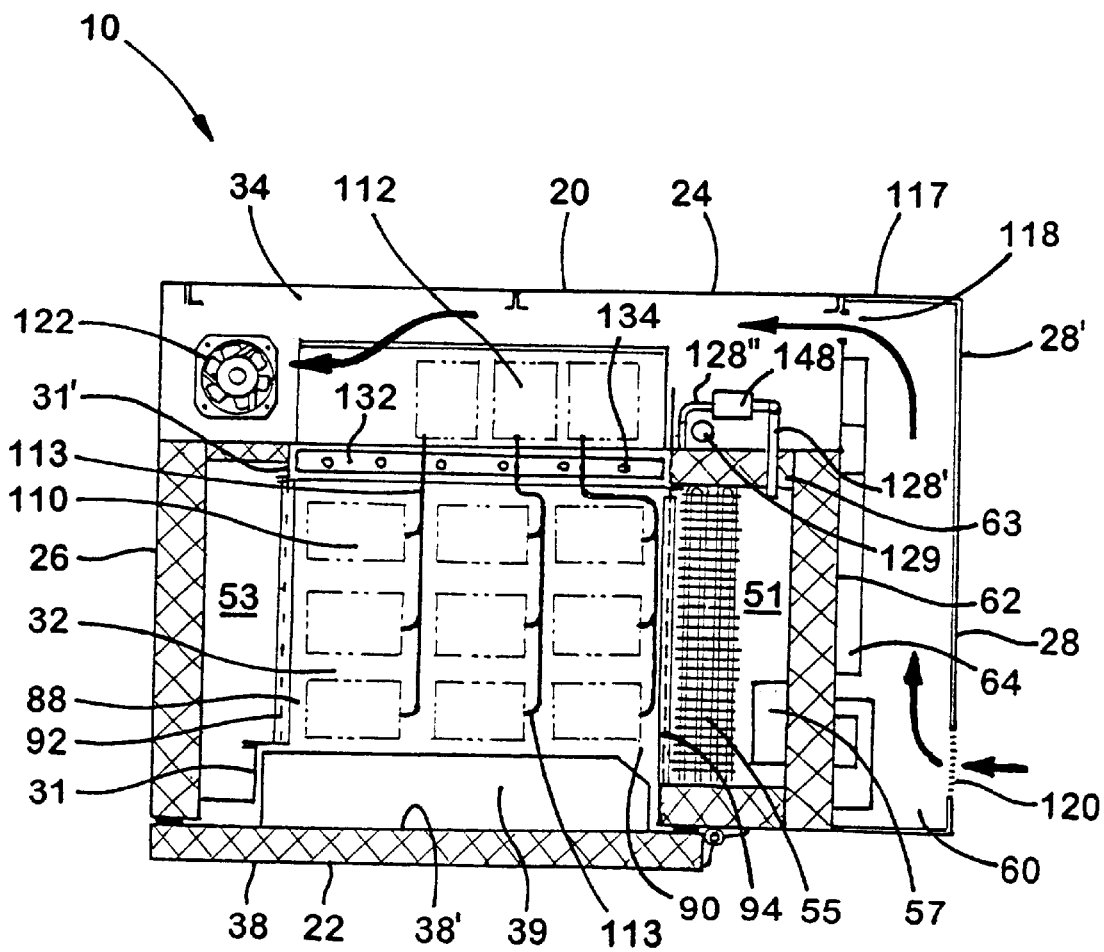
FIG. 4 is a sectional view taken along line IV—IV of FIG. 1.
Figure 5:
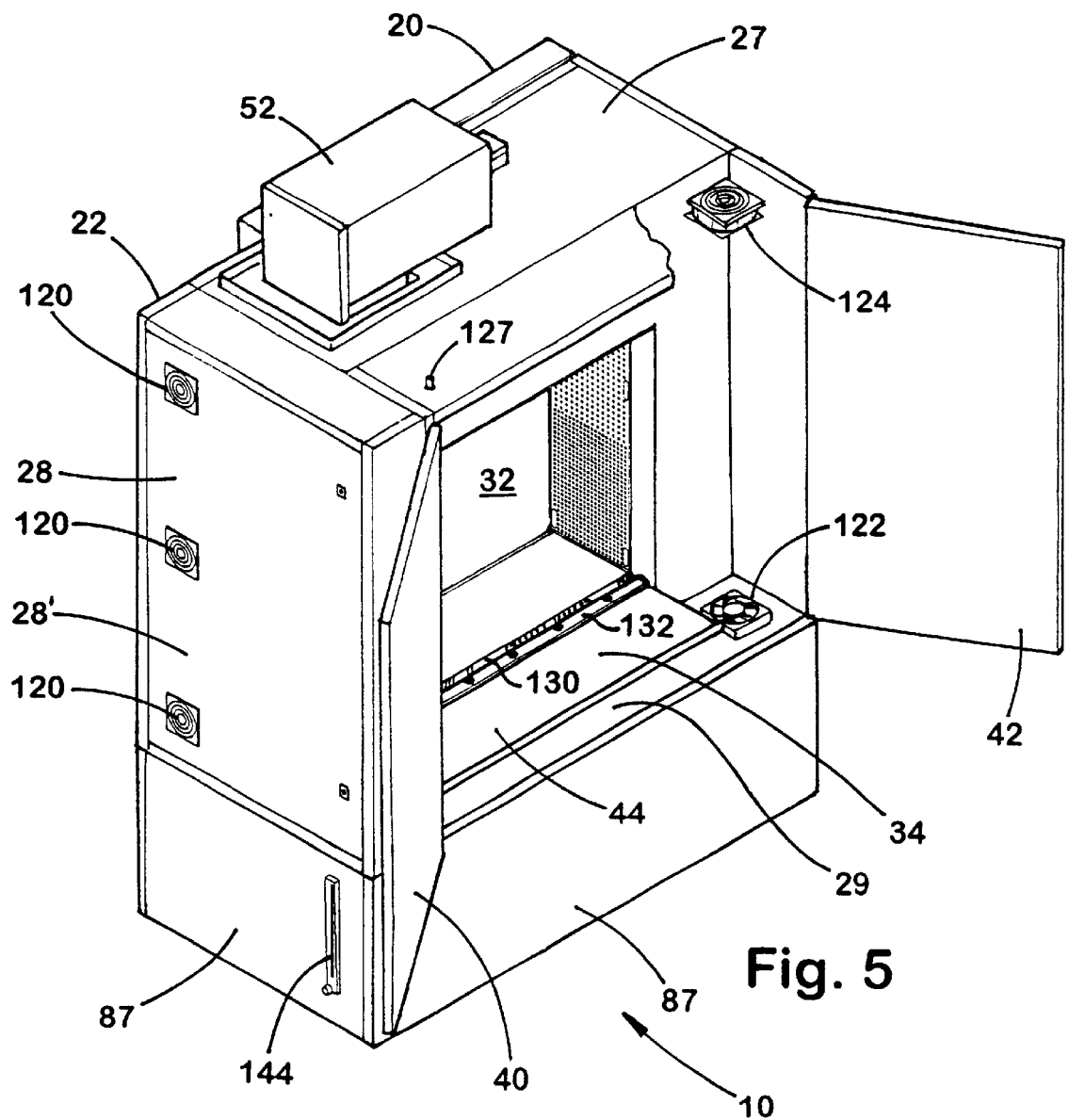
FIG. 5 is a rear, partially fragmented view of the environmental test chamber of FIGS. 1–4, depicting the fans of the air intake assembly.

The present invention advances an environmental test chamber for testing electronic components which provides a uniform airflow through the chamber which receives the electronic components. As used herein, the term "airflow" shall mean the rate of flow measured in mass or volume per unit time. Furthermore, the environmental test chamber provides an air intake assembly capable of providing an air current through both the control panel chamber and the second chamber. Moreover, the environmental test chamber of the present invention provides a pressurization device for pressurizing the partition to thereby prevent migration of air and moisture between the chambers. Although the following detailed description will make reference to the testing of hard drives for a computer system, it will be understood by those with ordinary skill in the art that the environmental test chamber of the present invention may be used to test other electrical components and other non-electrical components. Furthermore, those with ordinary skill in the art will recognize that the environmental test chamber of the present invention may be manufactured in various sizes to thereby accommodate electrical components having different dimensions.

Referring now to FIGS. 1 through 9, there is shown an environmental test chamber 10, according to a preferred embodiment of the invention. Environmental test chamber 10 includes a housing 20, that may be supported a preselected distance above the floor by a support 80. However, other means of support for housing 20 are possible. Support 80 includes a plurality of legs 82. Positioned between legs 82 are one or more horizontal members or shelves 84 on which a conditioning unit 86 is placed in order to condition the air within housing 20. The particular condensing unit 86 utilized may be any condenser normally utilized in the art providing the required temperature variation, given the dimensions of environmental test chamber 10. Non-limiting examples of a condensing unit 86 for use with the present invention include an air condenser or water cooled condenser. Attached to legs 82 are support panels 87, one or more of which are provided with air vents 89.

Housing 10 is formed with a front 22, back 24, and opposing sides 26 and 28. Interior 30 of housing 20 includes a main or first chamber 32, and an auxiliary or second chamber 34. First chamber 32 is dimensioned to accept a predetermined number of units which, in the illustrated embodiment, are computer hard drive units 110 or other electrical components. Hard drives 110 are stacked in a vertical array within first chamber 32. The number of hard drives 110 positioned within first chamber 32 varies as a function of the size of environmental test chamber 10 and the desired number of hard drives 110 to be tested. Second chamber 34 is separated from first chamber 32 by a partition 70. As will be discussed in detail below, partition 70 provides a physical barrier, preventing treated air present within first chamber 32 from entering second chamber 34. Second chamber 34 supports the testing electronic controls such as one or more central processing units ("CPUs") 112, maintained in electrical connection with hard drives 110. Electrical connection between hard drives 110 and CPUs 112 is established via electrical cables 113 placed through interstitial spaces defined in partition 70. During testing, CPUs 112 issue commands, resulting in the performance of certain operations by hard drives 110 under specified temperature and humidity conditions.

A front door 38 is attached to front 22 of housing 20 to thereby removably seal first chamber 32. Interior surface 38' of front door 38 is provided with a barrier 39. Barrier 39 maintains the airflow direction such that hard drives 110 gain maximum air exposure. A pair of rear doors 40, 42, hingedly attached to back 24 of housing 20, enclose second chamber 34. Second chamber 34 includes a horizontally disposed tray or shelf 44, positioned a preselected distance above bottom 29 of housing 20. CPUs 112 are positioned on shelf 44 and thereby maintained a preselected distance above bottom 29. Consequently, in the event moisture or water is collected within second chamber 34, the water will drain below shelf 44 and hence prevents water damage to CPUs 112.

A control panel chamber 60 is positioned in housing 20 and is exterior to both first chamber 32 and second chamber 34. Control panel chamber 60 is defined between front 22 and back 24 of housing 20, inner wall 62 and side 28 of housing 20. Control panel chamber 60 has positioned therein various electrical control devices 64 required to operate environmental test chamber 10. Control devices 64 are supported on inner wall 62. A side door 28' is hingedly connected to side 28 and allows access to control panel chamber 60. Control devices 64, positioned within control panel chamber 60, are in electrical connection with a controller 66 positioned in front 22 of housing 20. Controller 66 may be any controller normally utilized within the industry which permits an operator to control environmental test chamber 10.

An air circulation enclosure or plenum 50 surrounds first chamber 32. Plenum 50 is defined between the outer surfaces of first chamber 32, inner sidewall 62, side 26 and top 27 of housing 20. A jack shaft assembly 52 is supported by top 27 of housing 20 and depends a preselected distance within plenum 50. Jack shaft assembly 52 contains an air blower 54, positioned within plenum 50, which is configured to draw air from region 51 of plenum 50 and direct air towards region 53 of plenum 50. Air blower 54 may be any air blower commonly utilized in the art having the power required to generate a preselected fluid velocity. Positioned within region 51 of plenum 50 is an evaporator coil 55 and a dehumidifier coil 57. Both evaporation coil 55 and dehumidifier coil 57 are in operational connection with condensing unit 86. Additionally, a steam generator 56, supported by bottom 29 of housing 20, extends a preselected distance within region 51 of plenum 50. Steam generator 56 produces steam which is entrained within the airflow pattern developed by jack shaft assembly 52. A heater 58 is supported by, and depends from, top 27 of housing 20. Heater 58 depends a preselected distance within plenum 50, and alters the temperature of air circulating within plenum 50. Heater 58 may be any heater utilized in the art capable of heating the air within plenum 50 to a preselected temperature value.

First chamber 32 is configured with an exhaust area 88 through which air from region 53 of plenum 50 is exhausted into first chamber 32. Jack shaft assembly 52 draws air into region 51 of plenum 50 from the interior of first chamber 32 through an intake area 90, opposing exhaust area 88. Once evacuated from first chamber 32 via intake area 90, air residing within region 51 of plenum 50 is treated to condition the air to a preselected temperature and humidity by selectively activating evaporator coil 55, dehumidifier coil 57, and/or steam generator 56. Thereafter, the air may be further treated by activating heater 58. Selective activation of evaporator coil 55, steam generator 56, dehumidifier coil 57, and/or heater 58 is dictated by the desired temperature and humidity conditions of the preselected temperature/humidity schedule. Upon proper treatment, jack shaft assembly 52 transports the air into region 53 where it is recirculated into first chamber 32 via exhaust area 88.

Exhaust area 88 and intake area 90 of first chamber 32 are configured to provide a substantially uniform airflow through first chamber 32. Specifically, exhaust area 88 and intake area 90 provide a substantially uniform airflow pattern across the vertical cross section of first chamber 32. The substantially uniform airflow through first chamber 32 is achieved by equipping exhaust area 88 with a vertically positioned exhaust panel 92 and intake area 90 with a vertically positioned intake panel 94. Both exhaust panel 92 and intake panel 94 are formed having a plurality of throughholes 95, placed in spaced relation. Furthermore, both exhaust panel 92 and intake panel 94 are segmented into an upper or top region 96, a middle region 97 and a bottom or lower region 98. Within each region 96, 97 and 98, the size of throughholes 95, and/or the horizontal distance 99, and/or the vertical distance 99', between throughholes 95 is varied. Variation in the size of, and/or the horizontal or vertical distance between throughholes 95 permits control of the quantity of air exhausted into, and subsequently drawn from first chamber 32 such that the lower region 32', middle region 32" and upper region 32'" of first chamber 32 experience the same airflow. Altering the size of the throughholes 95, horizontal distance 99, or vertical distance 99' enables the selective control of the quantity of surface area through which air is exhausted into, and subsequently evacuated from, regions 32', 32" and 32'" of first chamber 32. The exact horizontal and vertical distance between throughholes 95 and the size of throughholes 95 within top region 96, middle region 97 and lower region 98, will depend on the desired airflow through first chamber 32 and is therefore application specific.

Figure 7:
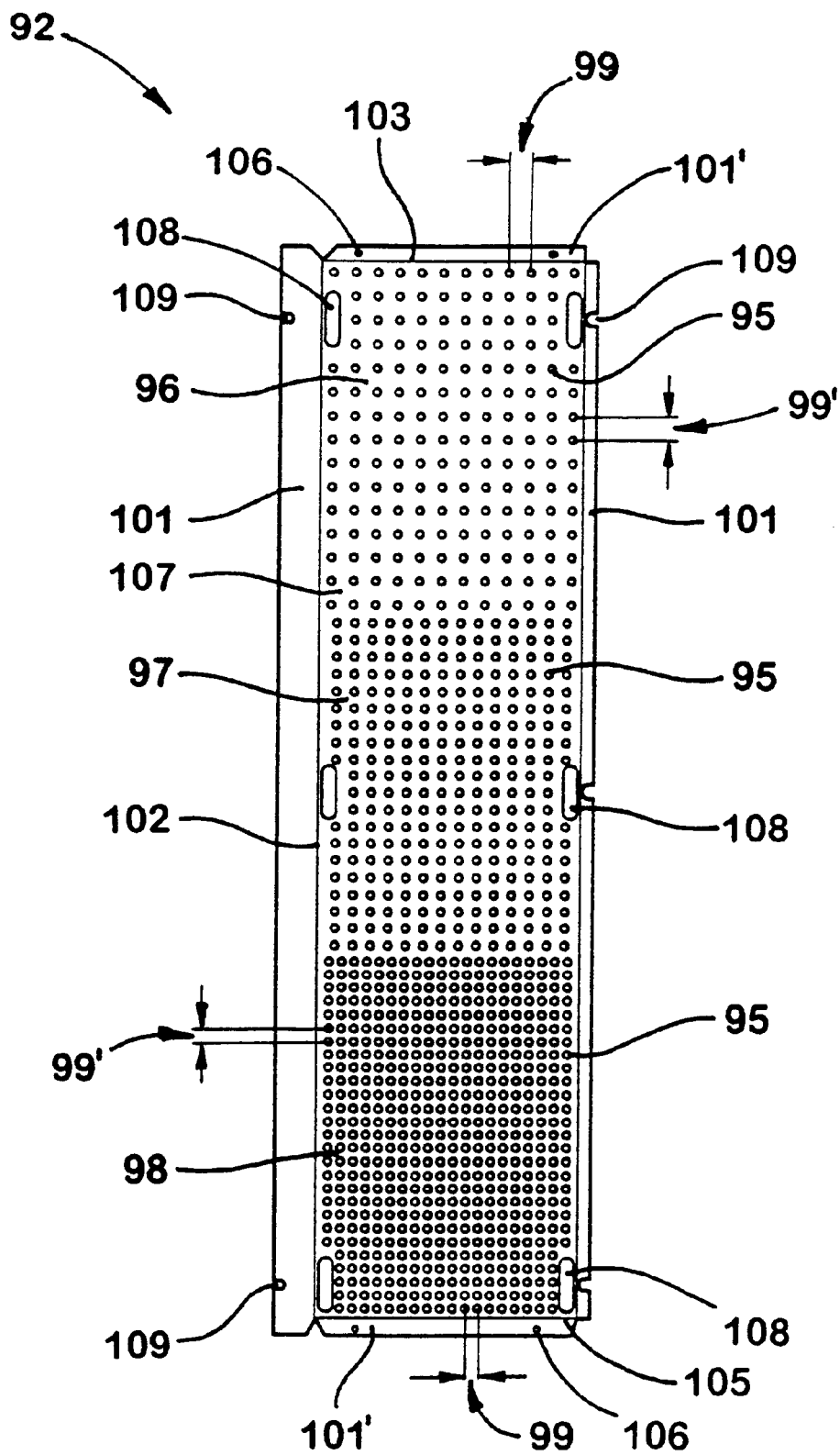
FIG. 7 is a front view of an exhaust panel according to the invention.
Figure 7A:
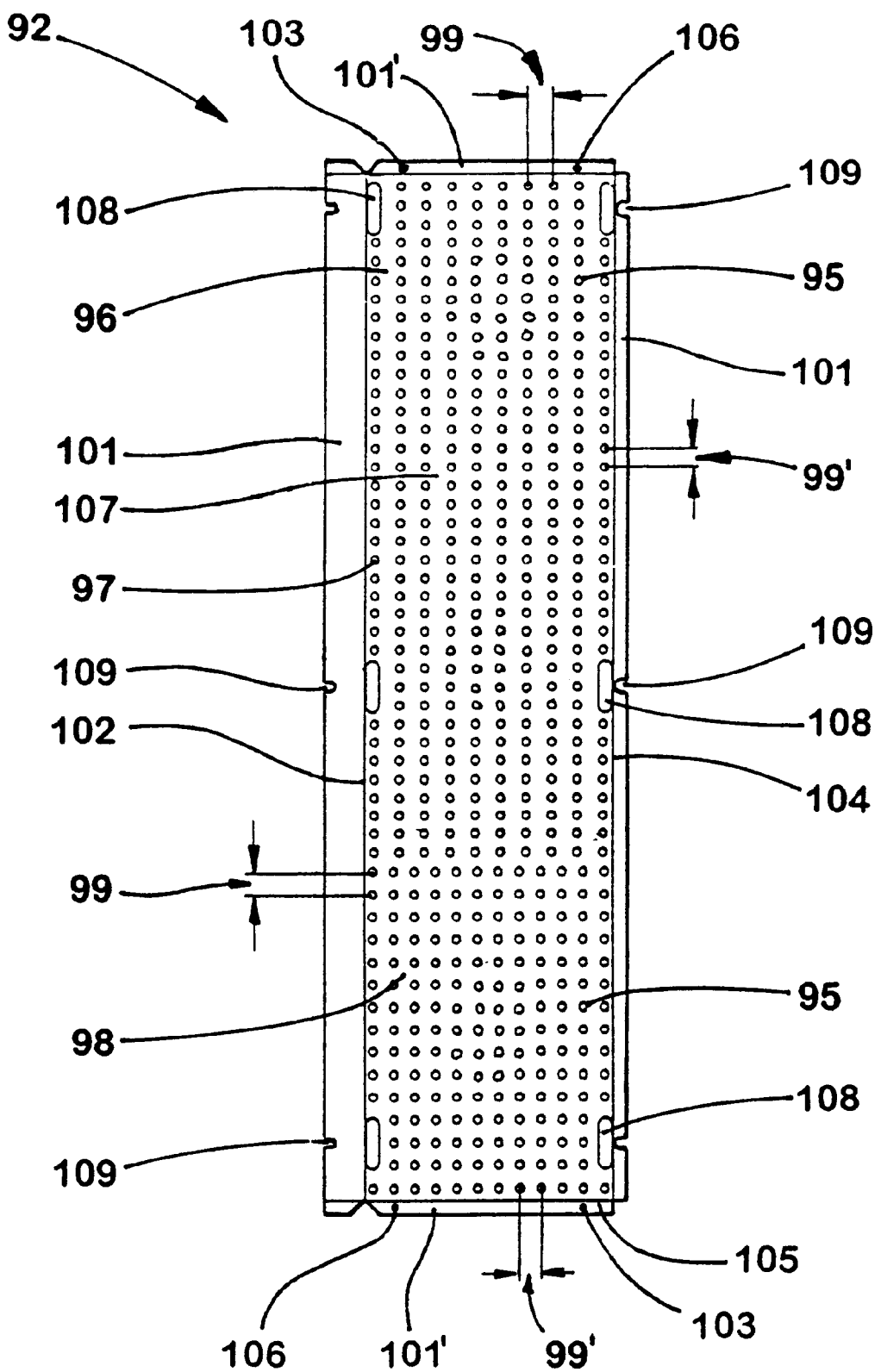
FIG. 7a is a front view of an exhaust panel according to an alternative preferred embodiment of the invention.
Figure 10:
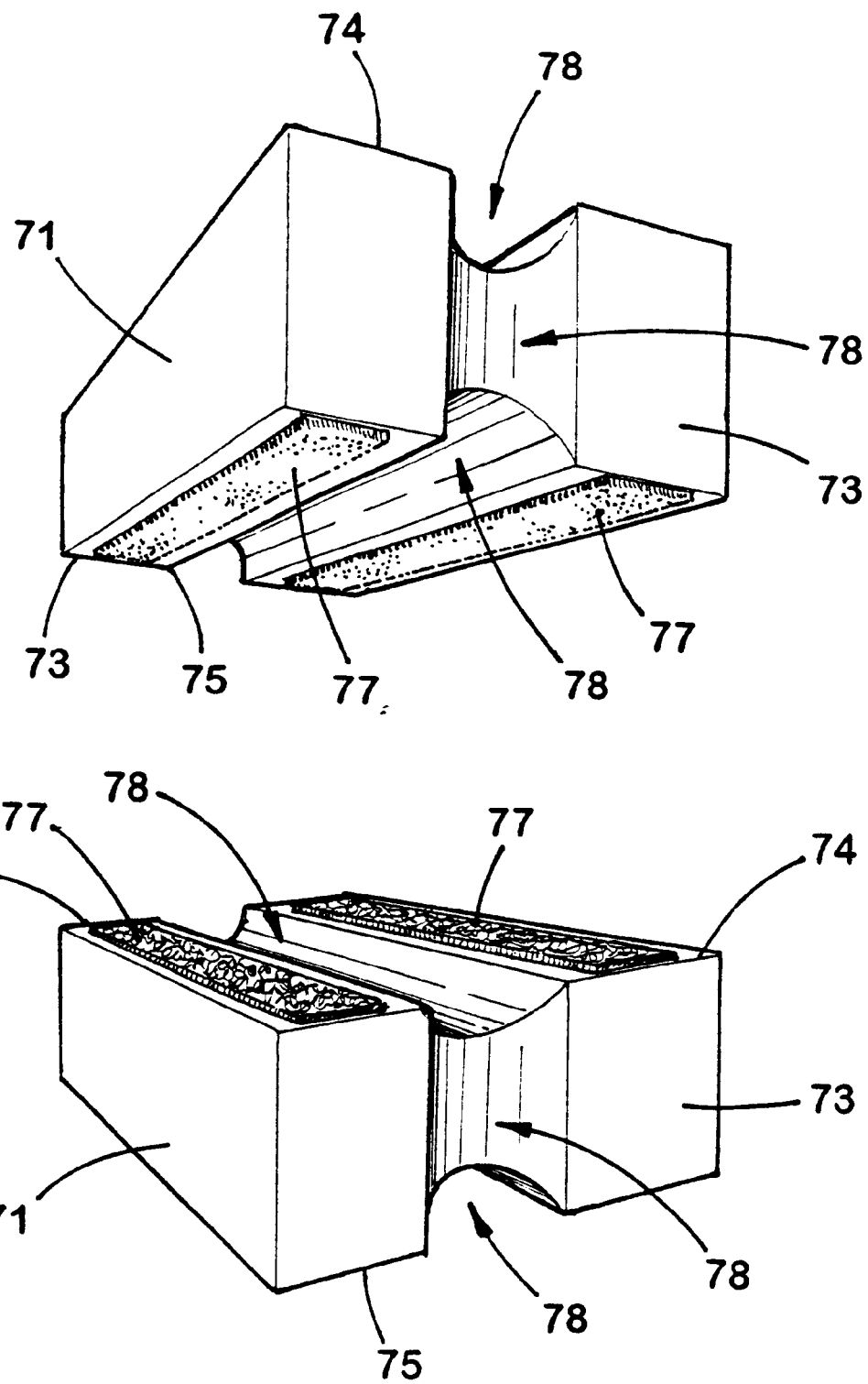
FIG. 10 is an exploded, perspective view of the bricks which define a partition used in the environmental test chamber of the present invention.
Figure 11:
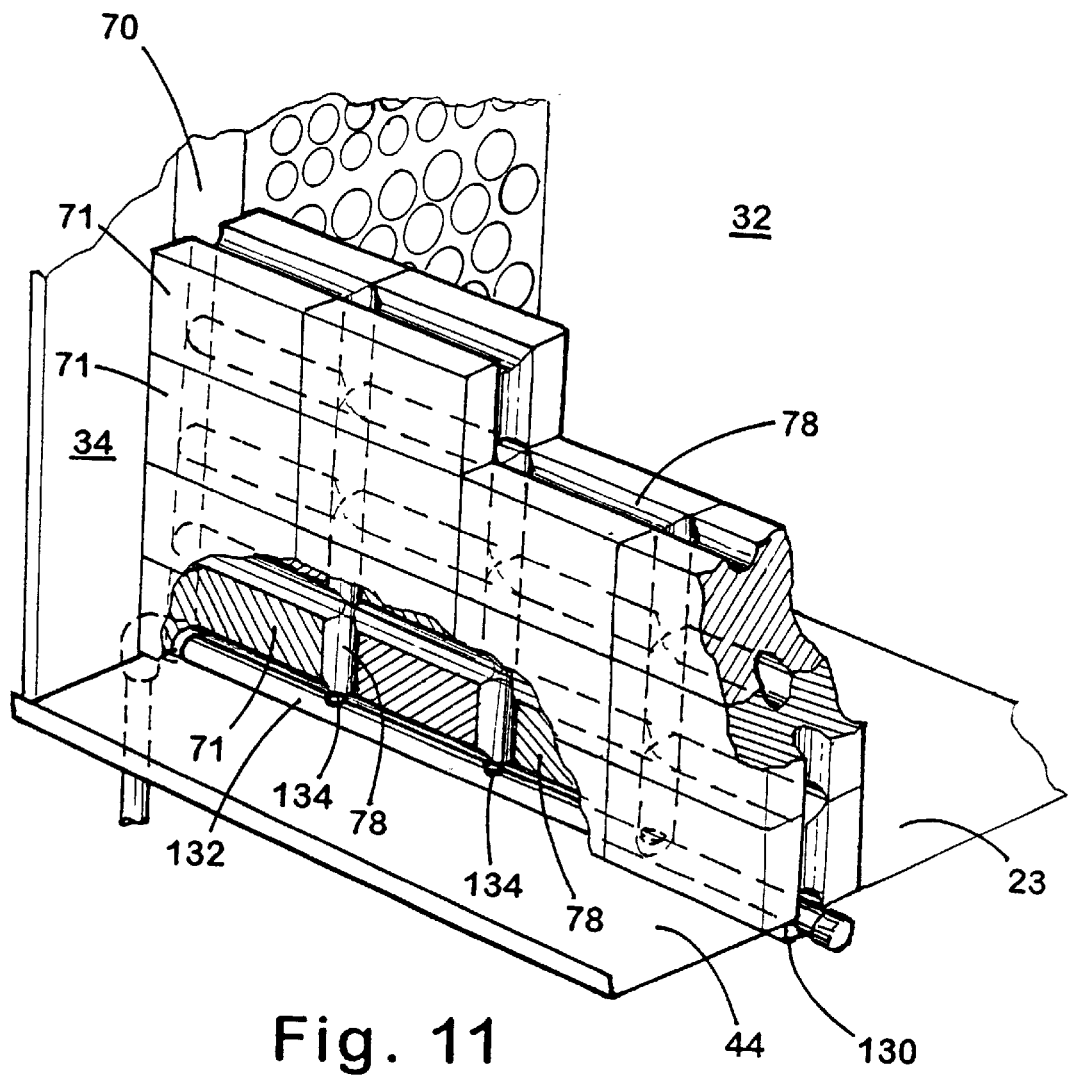
FIG. 11 is a detailed, fragmentary view of an air manifold according to the invention, illustrated positioned below the partition.

When plenum 50 has a general C-shape with a pair of vertical regions 51 and 53 which are in communication with intake panel 94 and exhaust panel 92, respectively, exhaust panel 92 may be configured such that horizontal distance 99 and vertical distance 99' between throughholes 95 are approximately equal in top region 96, middle region 97, and bottom region 98, while the size of throughholes 95 increases from top region 96 to bottom region 98. Furthermore each region 96, 97, 98 occupies approximately 33% of the height of exhaust panel 92. Preferably, as shown in FIG. 7a, the size of throughholes 95 in exhaust panel 92 remains approximately equal from top region 96 through bottom region 98. Horizontal distance 99 remains substantially equal in top region 96 and middle region 97, and decreases in bottom region 98. Vertical distance 99' decreases from top region 96 to middle region 97, while the vertical distance 99' in bottom region 98 is greater than the vertical distance 99' of top region 96 or middle region 97. Also, in this embodiment, middle region 97 occupies approximately 37% of the height of exhaust panel 92, while top region 96 occupies approximately 30%, and bottom region 98 approximately 33% of the height of exhaust panel 92. Furthermore, intake panel 94 may be configured such that the size of throughholes 95 increases from top region 96 to bottom region 98, while the distance 99 and 99' between throughholes 95 decreases from top region 96 to bottom region 98.

Exhaust panel 92 is formed with a flange 101 projecting from side 102 and 104. Top 103 and bottom 105 are formed with a flange 101'. Flange 101 extending from side 102 is of greater length than the flange 101 extending from side 104. Prior to installation, flanges 101 are bent to assume a generally orthogonal position with respect to face 107 of exhaust panel 92, to thereby enable exhaust panel 92 to be secured to members 31 and 31' projecting from the interior surface of side 26 of housing 20. Securement is achieved by the insertion of one or more bolts, or like fasteners through notches 109 formed in flanges 101 and throughholes 106 formed in flanges 101. Additionally, face 107 of exhaust panel 92 includes cut-out sections 108, permitting a wrench or like fastening device to be used in securing exhaust panel 92 to members 31 and 31'. Intake panel 94 is formed with a flange 114 projecting from the perimeter of intake panel 94. A plurality of throughholes 115 are attached to flange 114 to permit attachment between intake panel 94 and front 22 of housing 20 and inner wall 63, by bolts or like fasteners.

In an alternative preferred embodiment, as depicted in FIG. 9, intake panel 94 may be configured to have a bottom region 98 which is completely open. In this embodiment, top region 96 of intake panel 94 would be positioned in fluid communication with upper region 32'" of first chamber 32, and middle region 97 of intake panel 94 would be in fluid communication with middle region 32" of first chamber 32. Lower region 32' of first chamber 32 would be in direct fluid communication with region 51 of plenum 50 and would not be obstructed by a panel section. As jack shaft assembly 52 is located above region 51 of plenum 50, the least amount of vacuum is experienced in lower region 32' of first chamber 32. The absence of a panel section in intake area 90 corresponding to lower region 32' of first chamber 32 ensures a sufficient evacuation of air from lower region 32' of first chamber 32, to thereby maintain uniformity in airflow between lower region 32', middle region 32" and upper region 32'" of first chamber 32.

Environmental test chamber 10 is equipped with an air intake assembly which inducts air into control panel chamber 60 and forwards the same into second chamber 34 to provide ambient air to both control devices 64, positioned within control panel chamber 60, and CPUs 112 located within second chamber 34. The air intake assembly includes one or more air intake vents 120, and a pair of air blowers or fans 122 and 124 placed within second chamber 34. Air intake vents 120 are positioned within side door 28' of side 28, and are preferably positioned proximate to front 22 of housing 20. Air intake vents 120 are in fluid communication with control panel chamber 60. Fan 122 is secured to bottom 29, and exhausts air from second chamber 34 via an exhaust vent positioned in bottom 29 (not shown). Fan 124 depends from top 27 of housing 20 and exhausts air from second chamber 34 via an exhaust vent 126 positioned in top 27. In order to provide fluid communication between control panel chamber 60 and second chamber 34, a plurality of apertures or slots 118 are formed in a divider wall 117 which separates second chamber 34 from control panel chamber 60. In operation, fans 122 and 124 are actuated to pull a vacuum, resulting in the induction of air into control panel chamber 60 via air intake vents 120. The air is drawn over the electrical devices 64 positioned within control panel chamber 60 and approaches divider wall 117. Slots 118 permit air from control panel chamber 60 to enter second chamber 34. Once in second chamber 34, the ambient air reduces the temperature of CPU's 112 positioned on shelf 44. Thereafter, fans 122 and 124 exhaust the air to the atmosphere.

Figure 15:
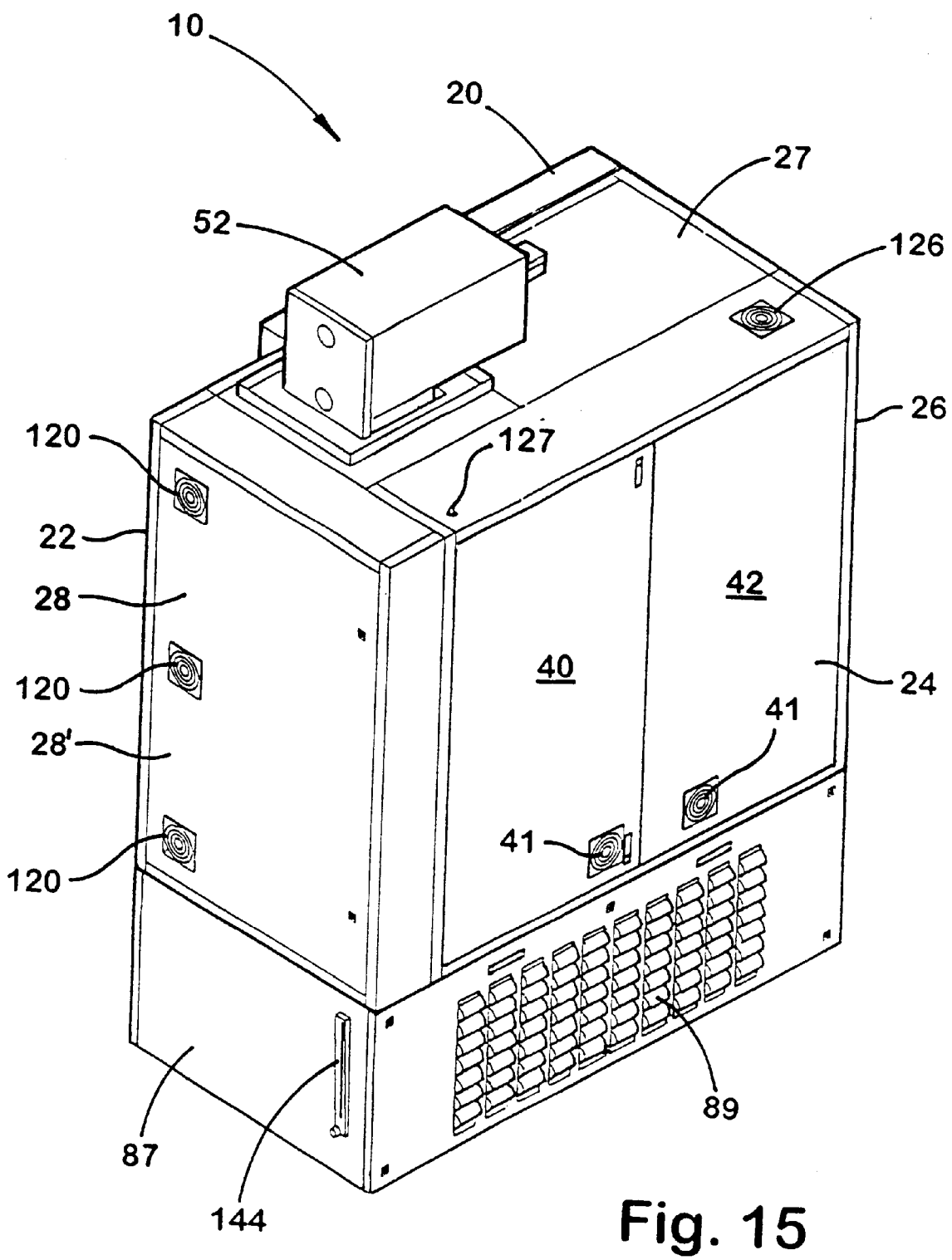
FIG. 15 is a rear perspective view of the environmental test chamber depicted in FIG. 14.
Figure 16:
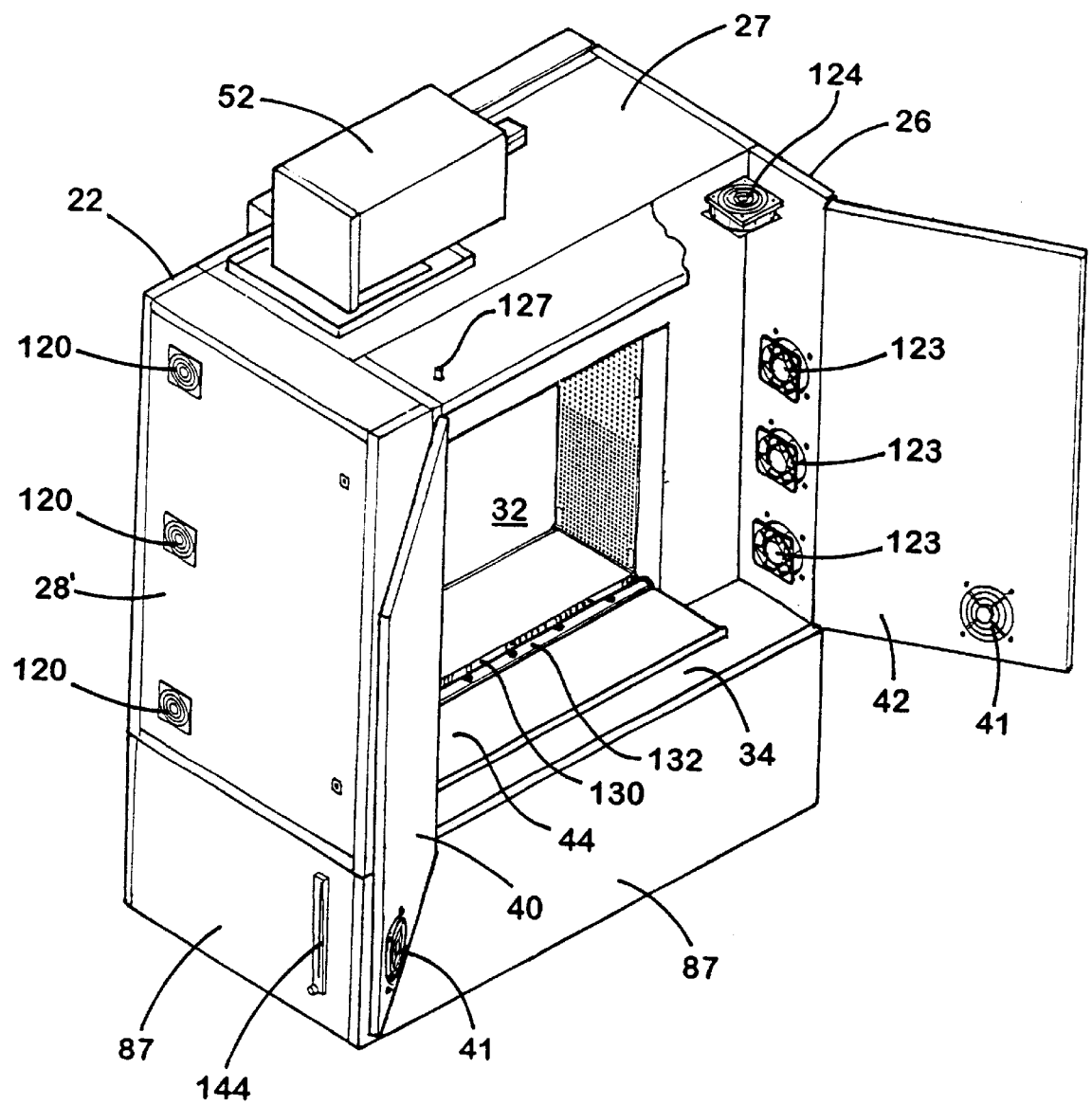
FIG. 16 is a rear, partially fragmented view of the environmental test chamber of FIGS. 14 and 15, depicting the fans of the air intake assembly.

As depicted in FIGS. 15 and 16, in order to increase the flow of air through second chamber 34, in a preferred embodiment, the air intake assembly further includes air vents 41, attached to rear doors 40, 42, and in fluid communication with second chamber 34. In the illustrated embodiment, a single vent 41 is attached to each rear door 40, 42. However, it will be appreciated that more than one vent 41 may be formed in each rear door 40, 42.

Figure 14:
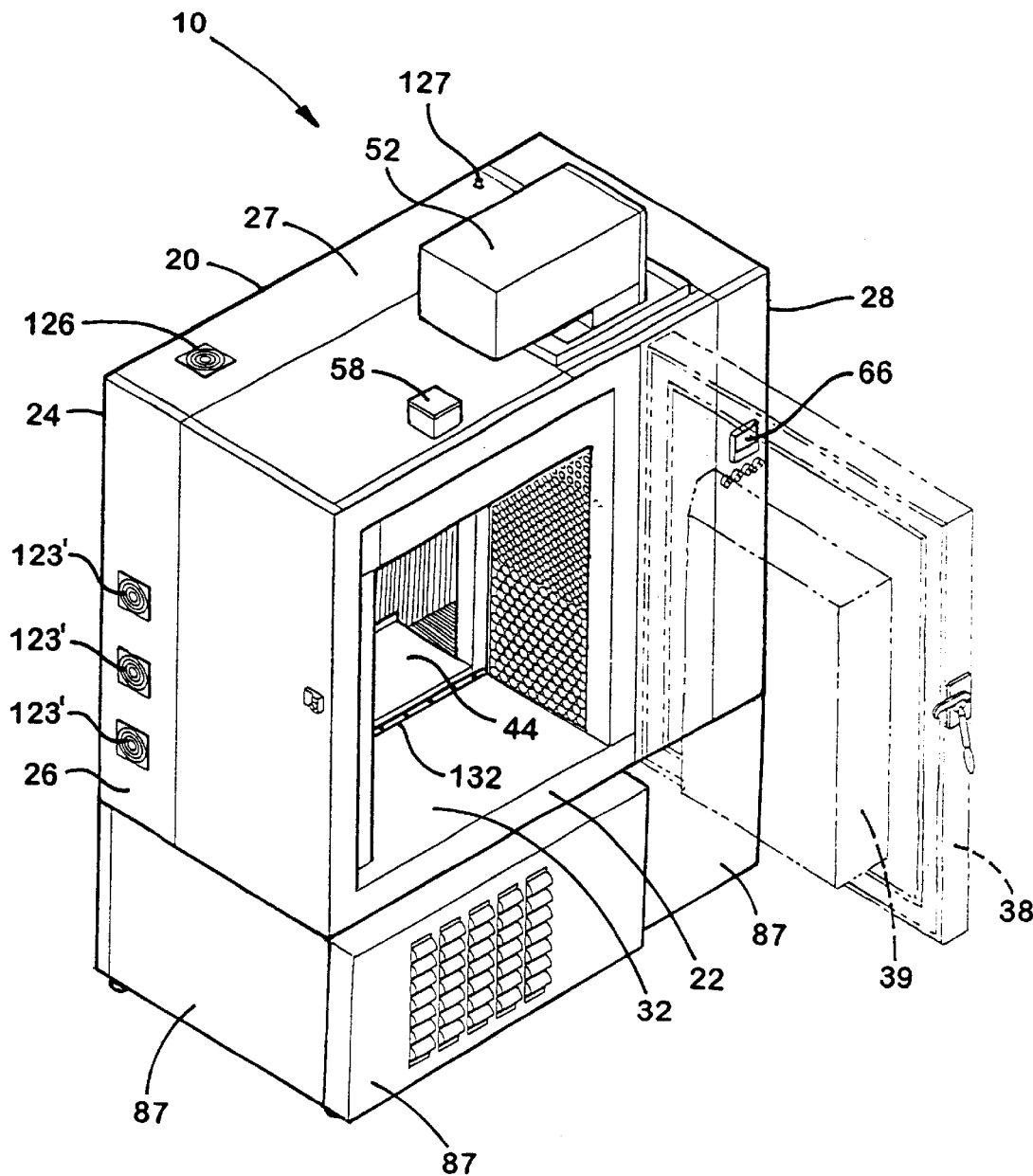
FIG. 14 is a front perspective view of an environmental test chamber according to an alternative preferred embodiment of the present invention, with the front door illustrated in phantom.

In an alternative preferred embodiment, as shown in FIGS. 14 and 16, second chamber 34 is equipped with fan 124, and at least one fan 123 mounted within second chamber 34, along side 26. In the illustrated embodiment, there are three fans 123, but it will be appreciated by those with ordinary skill in the art that less than three or more than three may be used without departing from the spirit and scope of the invention. Fan 124 and fans 123 draw air from control panel chamber 60, through slots 118, and over CPUs 112 positioned in second chamber 34. As shown in FIG. 14, fans 123 exhaust air to the atmosphere through vents 123' formed in side 26.

Turning now to FIGS. 10 through 13, partition 70 divides first chamber 32 from second chamber 34. Normally, partition 70 is composed of a plurality of foamed polymeric or composite bricks 71, stacked in a vertical array. Furthermore, opposing sides 73, top 74 and bottom 75 are equipped with complementary components of a hook-and-loop fastener 77 to provide interconnection between bricks 71. Electrical cables 113, attached to both CPUs 112 and hard drives 110, are passed through the interstices formed between adjacent bricks 71 of partition 70. Bricks 71 are further provided with a cutout section 78. Cutout section 78 is formed on opposing sides 74, top 75 and bottom 76. When stacked in a vertical arrangement, cutout section 78 of each brick 71 is in registration with the cutout section 78 of the adjacent brick 71. Preferably, cutout sections 78 are formed in an arcuate or semi-circular shape. When bricks 71 are in position, the cut-out sections 78 of each brick 71 forms a vertical and horizontal grid or lattice pattern through partition 70.

Figure 12:
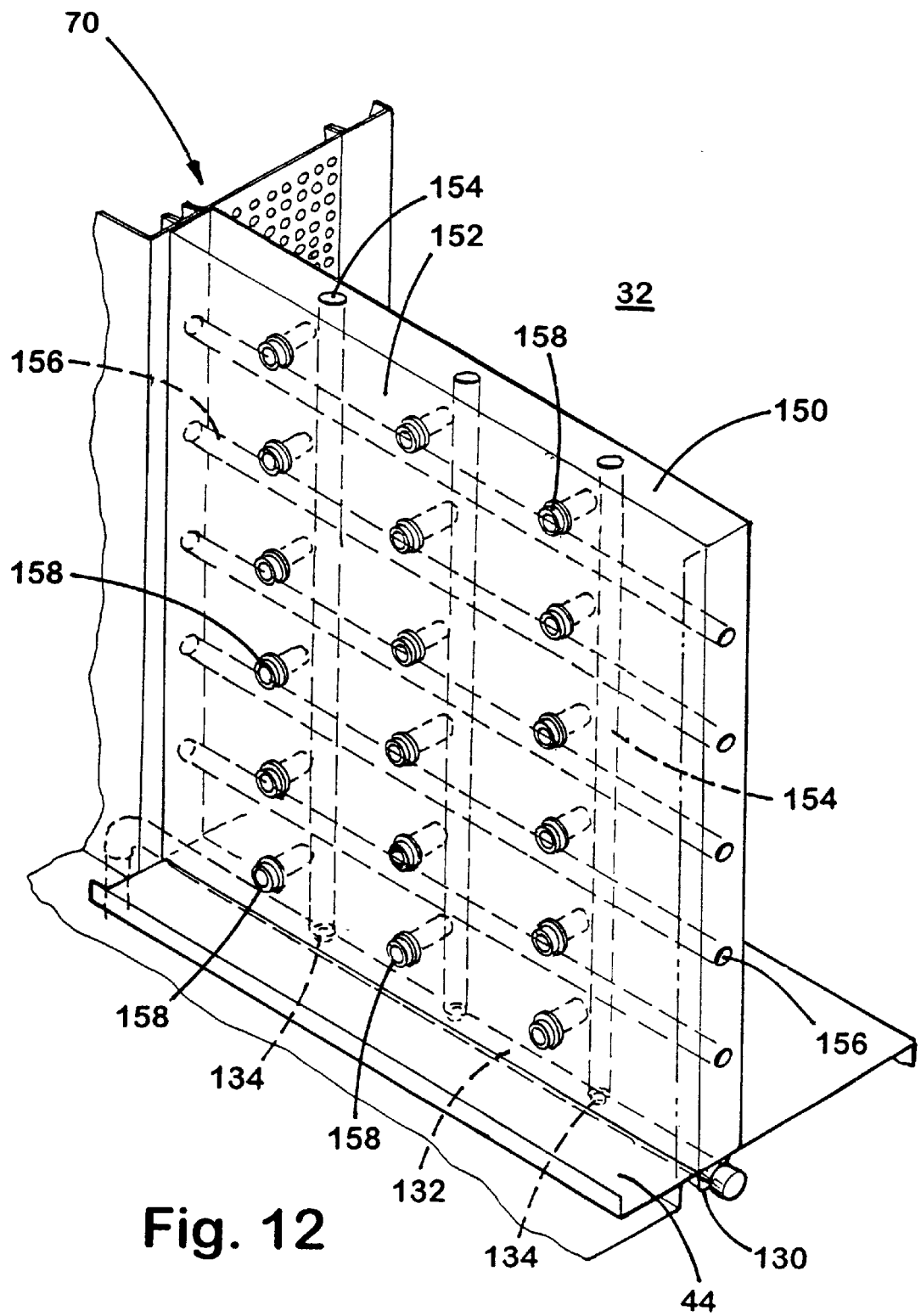
FIG. 12 is a detailed, fragmentary view of an air manifold according to the invention, illustrated positioned below the partition, wherein the partition is illustrated as a panel shown in phantom.
Figure 13:
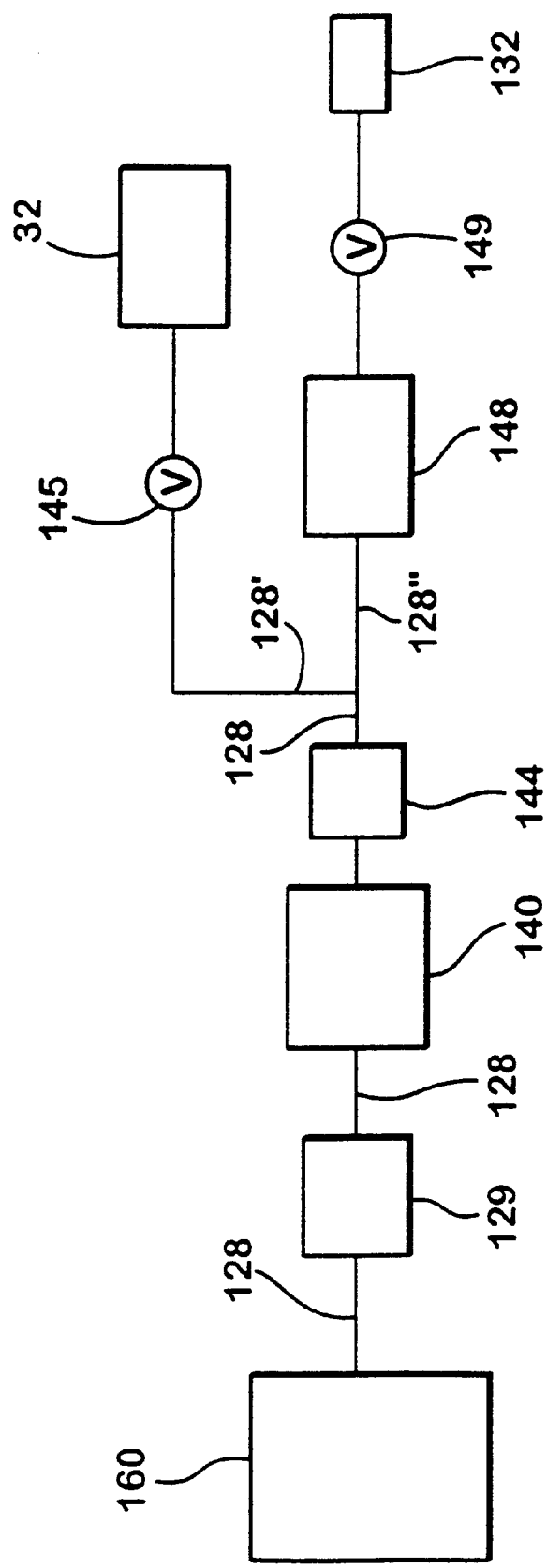
FIG. 13 is a diagrammatic representation of piping system in fluid communication with an air manifold, according to the present invention.

In a preferred embodiment, as shown in FIG. 12, partition 70 is formed of a single panel 150 of foamed polymeric or composite material. Panel 150 is dimensioned to frictionally engage the interior walls of housing 20 and thereby separate first chamber 32 from second chamber 34. Interior 152 of panel 150 is formed with a plurality of interconnected vertical and horizontal channels 154, 156, respectively. Vertical channels 154 and horizontal channels 156 form an internal grid or lattice of channels within panel 150. Panel 150 is formed having a plurality of electrical connectors 158 positioned therethrough. Electrical connectors 158 enable an electrical connection between CPUs 112 within second chamber 34 and hard drives 110 within first chamber 32 by attaching the cable from a CPU 112 and hard drive 110 to the opposing sides of an electrical connector 158.

Figure 6:
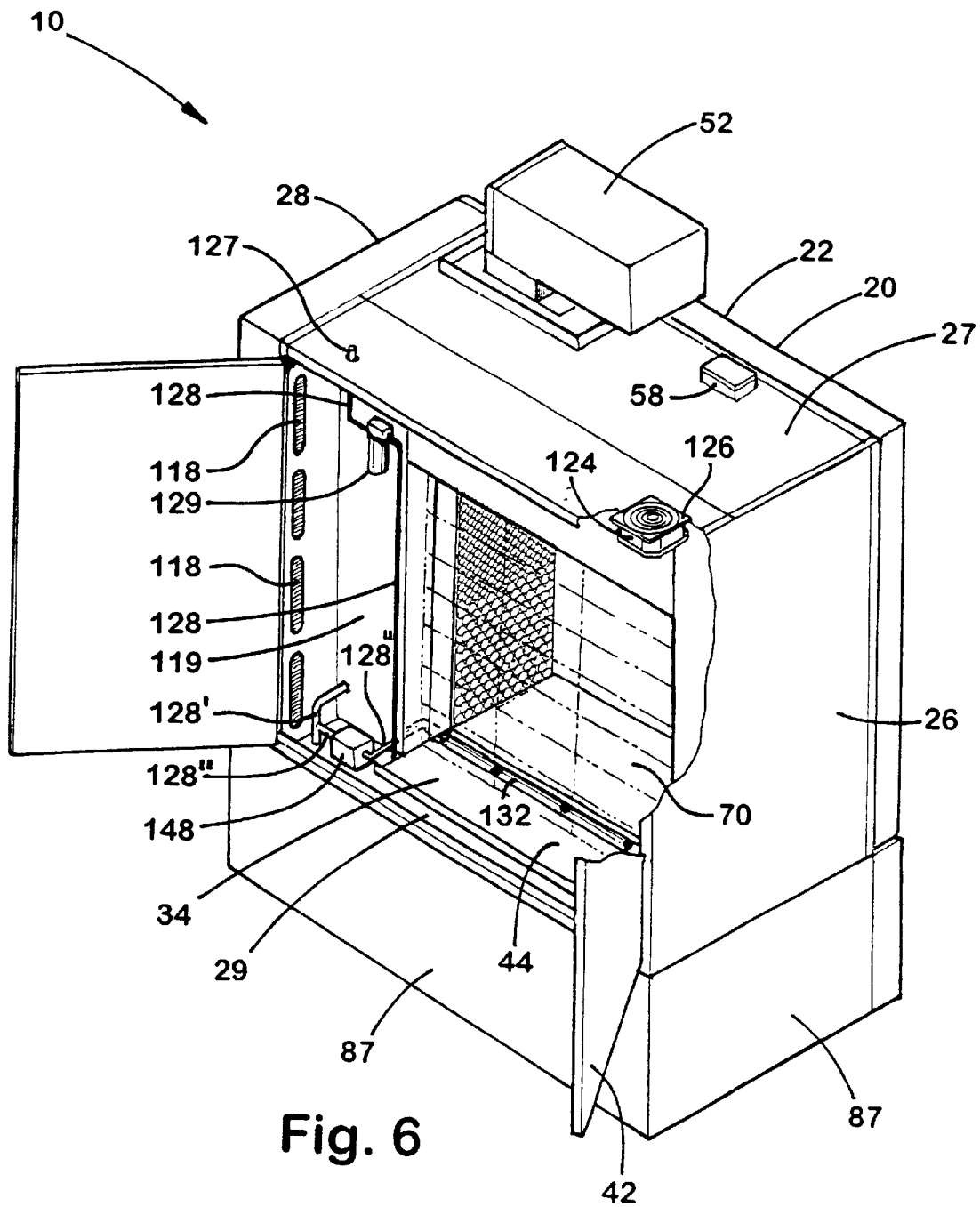
FIG. 6 is a rear, partially fragmented view of the environmental test chamber of FIGS. 1–5, depicting the slots positioned within the divider wall.

A channel 130 is formed within floor 23 of housing 20. Channel 130 is positioned generally perpendicular to sides 26 and 28 of housing 20. Bricks 71 or panel 150 is positioned directly over channel 130. An air manifold 132 is dimensioned to be received by channel 130. Formed along the upper periphery of air manifold 132 are a plurality of exhaust holes 134, placed in spaced relation. Exhaust holes 134 are positioned in registration with cutout sections 78 formed in bricks 71 or vertical channels 154 of panel 150. Air manifold 132 is in fluid communication with an air inlet 127 positioned within top 27 of housing 20. A source of pressurized air 160 is connected to inlet 127. When activated, pressurized air is forwarded through air inlet 127 and transported via piping 128 to a filter 129 supported by wall 119 (FIG. 6). Filter 129 removes oil and other particulates from the pressurized air stream. Once the air is filtered, it is further transported via piping 128 to a dry air purge 140 which dries the air. Dry air purge 140 may be any device commonly utilized in the art to dry a gas stream. Thereafter the dried, pressurized air is forwarded to a flowmeter 144 for monitoring the volumetric flow rate of the air stream. The air stream is then bifurcated, or branched, by piping 128' and 128". Air within piping 128' is controllably exhausted into first chamber 32 by a valve 145. Valve 145 may be a solenoid valve or other valve commonly employed in the art. Air from piping 128' enters first chamber 32 through exhaust port 146 (FIG. 3), and provides an additional source of dehumidified air in order to control the environmental conditions of first chamber 32. Air in piping 128" is forwarded to a heater 148 and heated to a preselected temperature. Thereafter, the heated, pressurized air is controllably released into air manifold 132 through a valve 149. Valve 149 may be a solenoid valve or other valve commonly employed in the art. Injection of dried, pressurized air into cutout section 78 of bricks 71 pressurizes partition 70, resulting in a seal between bricks 71. This seal prevents the migration of moisture of air between the chambers 32, 34 via the interstices between bricks 71, and thereby maintains the environmental conditions of each chamber 32, 34 at their desired levels.

When air manifold 132 is used in conjunction with panel 150, the injection of dry, heated, pressurized air into panel 150 increases the insulative ability of panel 150 to thereby maintain the humidity and temperature conditions of each chamber 32, 34. Additionally, the air from air manifold 132 pressurizing the interstices surrounding electrical connectors 158 and consequently minimizes the undesired migration of air and moisture between first chamber 32 and second chamber 34.

Changes and modifications to the specifically described embodiments can be carried out without the departing from the principals of the invention, which is intended to be limited only by the scope of the appended claims, as interpreted according to the principals of patent law including the doctrine of equivalents.

The embodiments of the invention in which an exclusive property or privilege is claimed are defined as follows:

1. An environmental test chamber comprising a housing defining a chamber having a vertical cross section, said chamber having an exhaust region through which air is exhausted into said chamber, and an intake region through which air is evacuated from said chamber, wherein said exhaust region and said intake region are configured to provide a substantially uniform airflow across said vertical cross section of said chamber.

2. The environmental test chamber as recited in claim 1, wherein said exhaust region and said intake region are configured with a non-uniform surface area through which air enters into, and is removed from said chamber to thereby provide a substantially uniform airflow through said vertical cross section of said chamber.

3. The environmental test chamber as recited in claim 2, wherein said exhaust region is formed having at least two sections, wherein each section of said at least two sections has a surface area through which air enters said chamber, wherein said surface area for said each section of said at least two sections is not equal.

4. The environmental test chamber as recited in claim 2, wherein said intake region is formed having at least two sections, wherein each section of said at least two sections has a surface area through which air is removed from said chamber, wherein said surface area for said each section of said at least two sections is not equal.

5. The environmental test chamber as recited in claim 1, wherein said chamber further comprises:
    an exhaust panel positioned in said exhaust region; and
    an intake panel positioned in said intake region.

6. The environmental test chamber as recited in claim 5, wherein said exhaust panel has at least two sections, wherein each section of said at least two sections of said exhaust panel is formed having a surface area through which air enters said chamber, wherein said surface area for said each section of said at least two sections is not equal.

7. The environmental test chamber as recited in claim 5, wherein said intake panel has at least two sections, wherein each section of said at least two sections of said intake panel is formed having a surface area through which air enters said chamber, wherein said surface area for said each section of said at least two sections is not equal.

8. The environmental test chamber as recited in claim 5, wherein said exhaust panel further comprises:
    a bottom region, said bottom region having a plurality of first apertures placed a preselected first horizontal distance apart and a preselected first vertical distance apart, each first aperture of said plurality of first apertures having a first diameter;
    a middle region, said middle region having a plurality of second apertures placed a preselected second horizontal distance apart and a preselected second vertical distance apart, each second aperture of said plurality of second apertures having a second diameter; and a top region, said top region having a plurality of third apertures placed a preselected third horizontal distance apart and a preselected third vertical distance apart, each third aperture of said plurality of third apertures having a third diameter.

9. The environmental test chamber as recited in claim 8, wherein said first diameter is approximately equal to said second diameter, and said second diameter is approximately equal to said third diameter, wherein said first horizontal distance is less than said second horizontal distance and said second horizontal distance is less than said third horizontal distance.

10. The environmental test chamber as recited in claim 8, wherein said first diameter is greater than said second diameter, and said second diameter is greater than said third diameter, wherein said first horizontal distance is approximately equal to said second horizontal distance and said second horizontal distance is approximately equal to said third horizontal distance.

11. The environmental test chamber as recited in claim 8, wherein said first diameter is greater than said second diameter, and said second diameter is greater than said third diameter, wherein said first horizontal distance is less than said second horizontal distance and said second horizontal distance is less than said third horizontal distance.

12. The environmental test chamber as recited in claim 8, wherein said first diameter is approximately equal to said second diameter and said second diameter is approximately equal to said third diameter, wherein said first vertical distance is less than said second vertical distance and said second vertical distance is less than said third vertical distance.

13. The environmental test chamber as recited in claim 8, wherein said first diameter is greater than said second diameter, and said second diameter is greater than said third diameter, wherein said first vertical distance is approximately equal to said second vertical distance and said second vertical distance is approximately equal to said third vertical distance.

14. The environmental test chamber as recited in claim 8, wherein said first diameter is greater than said second diameter, and said second diameter is greater than said third diameter, wherein said first vertical distance is less than said second vertical distance and said second vertical distance is less than said third vertical distance.

15. The environmental test chamber as recited in claim 5, wherein said intake panel further comprises:

a bottom region, said bottom region having a plurality of first apertures placed a preselected first horizontal distance apart and a preselected first vertical distance apart, each first aperture of said plurality of first apertures having a first diameter;

a middle region, said middle region having a plurality of second apertures placed a preselected second horizontal distance apart and a preselected second vertical distance apart, each second aperture of said plurality of second apertures having a second diameter; and a top region, said top region having a plurality of third apertures placed a preselected third horizontal distance apart and a preselected third vertical distance apart, each third aperture of said plurality of third apertures having a third diameter.

16. The environmental test chamber as recited in claim 15, wherein said first diameter is approximately equal to said second diameter, and said second diameter is approximately equal to said third diameter, wherein said first horizontal distance is less than said second horizontal distance and said second horizontal distance is less than said third horizontal distance.

17. The environmental test chamber as recited in claim 15, wherein said first diameter is greater than said second diameter, and said second diameter is greater than said third diameter, wherein said first horizontal distance is approximately equal to said second horizontal distance and said second horizontal distance is approximately equal to said third horizontal distance.

18. The environmental test chamber as recited in claim 15, wherein said first diameter is greater than said second diameter, and said second diameter is greater than said third diameter, wherein said first horizontal distance is less than said second horizontal distance and said second horizontal distance is less than said third horizontal distance.

19. The environmental test chamber as recited in claim 15, wherein said first diameter is approximately equal to said second diameter, and said second diameter is approximately equal to said third diameter, wherein said first vertical distance is less than said second vertical distance and said second vertical distance is less than said third vertical distance.

20. The environmental test chamber as recited in claim 15, wherein said first diameter is greater than said second diameter, and said second diameter is greater than said third diameter, wherein said first vertical distance is approximately equal to said second vertical distance and said second vertical distance is approximately equal to said third vertical distance.

21. The environmental test chamber as recited in claim 15, wherein said first diameter is greater than said second diameter, and said second diameter is greater than said third diameter, wherein said first vertical distance is less than said second vertical distance and said second vertical distance is less than said third vertical distance.

22. The environmental test chamber as recited in claim 5, wherein said intake panel further comprises:

a lower region, said lower region having a plurality of first apertures placed a preselected first horizontal distance apart and a preselected first vertical distance apart, each first aperture of said plurality of first apertures having a first diameter; and an upper region, said upper region having a plurality of second apertures placed a preselected second horizontal distance apart and a preselected second vertical distance apart, each second aperture of said plurality of second apertures having a second diameter.

23. The environmental test chamber as recited in claim 22, wherein said first diameter is approximately equal to said second diameter, and wherein said first horizontal distance is less than said second horizontal distance.

24. The environmental test chamber as recited in claim 22, wherein said first diameter is greater than said second diameter, and wherein said first horizontal distance is approximately equal to said second horizontal distance.

25. The environmental test chamber as recited in claim 22, wherein said first diameter is greater than said second diameter, and wherein said first horizontal distance is less than said second horizontal distance.

26. The environmental test chamber as recited in claim 22, wherein said first diameter is approximately equal to said second diameter, and wherein said first vertical distance is less than said second vertical distance.

27. The environmental test chamber as recited in claim 22, wherein said first diameter is greater than said second diameter, and wherein said first vertical distance is approximately equal to said second vertical distance.

28. The environmental test chamber as recited in claim 22, wherein said first diameter is greater than said second diameter, and wherein said first vertical distance is less than said second vertical distance.

29. The environmental test chamber as recited in claim 22, wherein said first chamber has a lower region, a middle region and an upper region, wherein said upper region of said exhaust panel is positioned in said upper region of said first chamber, and wherein said lower region of said exhaust panel is positioned within said middle region of said first chamber.

30. The environmental test chamber as recited in claim 1, wherein said chamber has a first sidewall and an opposing second sidewall, wherein said exhaust panel is positioned in said first sidewall, and wherein said intake panel is positioned in said second sidewall.

31. The environmental test chamber as recited in claim 1, wherein said chamber has a bottom region, a middle region and a top region, and wherein said exhaust region and said intake region are configured such that the airflow from said exhaust region to said intake region in said top region is substantially equal to the airflow in said middle region and said bottom region.

32. The environmental test chamber as recited in claim 1, further comprising a support depending from said housing, said support supporting said housing a preselected distance above the floor.

33. An environmental test chamber comprising a housing defining a first chamber, a second chamber, a control panel chamber positioned exterior to said first chamber and in fluid communication with said second chamber, and an air intake assembly carried by said housing, said air intake assembly providing an airflow through said control panel chamber and said second chamber.

34. The environmental test chamber as recited in claim 33, wherein said air intake assembly further comprises:
at least one vent in fluid communication with said control panel chamber; and
at least one fan in fluid communication with said second chamber, said at least one fan drawing air through said control panel chamber and into said second chamber.

35. The environmental test chamber as recited in claim 34, wherein said housing further comprises at least one rear door enclosing said second chamber and said air intake assembly further comprises at least one vent positioned in said at least one rear door.

36. The environmental test chamber as recited in claim 33, wherein said housing further comprises a control panel door, said at least one vent positioned in said control panel door.

37. The environmental test chamber as recited in claim 33, wherein said at least one fan is positioned within said second chamber.

38. The environmental test chamber as recited in claim 33, further comprising a divider wall between said second chamber and said control panel chamber, said divider wall having at least one slot formed therein.

39. The environmental test chamber as recited in claim 37, wherein said housing further comprises a sidewall opposing said divider wall, and wherein said air intake assembly further comprises at least one fan positioned in said second chamber and supported by said sidewall.

40. The environmental test chamber as recited in claim 33, wherein said second chamber has a top and a bottom, and wherein said at least one fan is a first fan depending from said top of said second chamber, and a second fan extending from said bottom of said second chamber.

41. The environmental test chamber as recited in claim 38, further comprising a horizontal tray positioned in said second chamber, said tray positioned a preselected distance above said bottom.

42. The environmental test chamber as recited in claim 33, wherein said first chamber has a vertical cross section, wherein said first chamber further comprises:
an exhaust region through which air is exhausted into said first chamber; and
an intake region through which air is evacuated from said first chamber,
wherein said exhaust region and said intake region are configured to provide a substantially uniform airflow across said vertical cross section of said first chamber.

43. The environmental test chamber as recited in claim 33, further comprising a pressurized partition, said pressurized partition separating said first chamber from said second chamber.

44. An environmental test chamber having a first chamber and a second chamber separated by a partition formed having a plurality of vertical air channels interconnected with a plurality of horizontal air channels, said environmental test chamber comprising an air manifold formed with a plurality of air holes, wherein each air hole of said plurality of air holes is in registration with a vertical air channel of the plurality of vertical air channels, said air manifold injecting air within the vertical air channels to thereby pressurize the partition.

45. The pressurization device as recited in claim 44, further comprising a source of pressurized air in fluid communication with said air manifold, said air manifold injecting pressurized air within the vertical air channels to thereby pressurize the partition.

46. The pressurization device as recited in claim 44, further comprising a dry air purge in fluid communication with said air manifold, said air manifold injecting dry air within the vertical air channels to thereby pressurize the partition.

47. The pressurization device as recited in claim 44, wherein the environmental test chamber is formed with a channel positioned below the partition, wherein said air manifold is positioned in said channel.

48. The pressurization device as recited in claim 44, further comprising a heater in fluid communication with said air manifold, said air manifold injecting heated air within the vertical air channels to thereby pressurize the partition.

49. The pressurization device as recited in claim 48, wherein the partition is a panel.

50. An environmental test chamber comprising a housing defining a chamber having a vertical cross section, said chamber having an exhaust region through which air is exhausted into said chamber, and an intake region through which air is evacuated from said chamber, an exhaust panel positioned in said exhaust region and an intake panel positioned in said intake region, wherein said exhaust panel and said intake panel each have at least a first section and a second section and a plurality of throughholes formed in said first section and said second section, wherein the distance between said throughholes formed in said first section is not equal to the distance between said throughholes formed in said second section to thereby provide a substantially uniform airflow across said vertical cross section of said chamber.

* * * * *